US011589885B2

(12) United States Patent
Fleury et al.

(10) Patent No.: US 11,589,885 B2
(45) Date of Patent: Feb. 28, 2023

(54) SYSTEMS AND RELATED METHODS FOR TISSUE TREATMENT

(71) Applicant: Boston Scientific Scimed, Inc., Maple Grove, MN (US)

(72) Inventors: Sean P. Fleury, Minneapolis, MN (US); Gregory Lee, Eden Prairie, MN (US); Eric Wespi, Maple Grove, MN (US); Brian Hanson, Shoreview, MN (US); Anthony Tassoni, Jr., Andover, MN (US); Nicholas Tassoni, Andover, MN (US); Jose A. Meregotte, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 858 days.

(21) Appl. No.: 16/452,851

(22) Filed: Jun. 26, 2019

(65) Prior Publication Data

US 2020/0000489 A1 Jan. 2, 2020

Related U.S. Application Data

(60) Provisional application No. 62/690,622, filed on Jun. 27, 2018.

(51) Int. Cl.
*A61B 17/32* (2006.01)
*A61B 1/273* (2006.01)

(52) U.S. Cl.
CPC ...... *A61B 17/320016* (2013.01); *A61B 1/273* (2013.01); *A61B 2017/320052* (2013.01)

(58) Field of Classification Search
CPC ......... A61B 17/320016; A61B 17/326; A61B 2017/320082
See application file for complete search history.

(56) References Cited

U.S. PATENT DOCUMENTS

| 7,338,505 | B2 * | 3/2008 | Belson | A61B 1/005 |
| | | | | 606/151 |
| 9,295,470 | B2 | 3/2016 | Baur et al. | |
| 9,743,931 | B2 * | 8/2017 | Grönberg | A61B 17/11 |
| 2005/0216040 | A1 * | 9/2005 | Gertner | A61F 5/0086 |
| | | | | 606/151 |

OTHER PUBLICATIONS

Vitali, Francesco, et al. "Endoscopic Full-Thickness Resection with an over-the-Scope Clip Device (FTRD) in the Colorectum: Results from a University Tertiary Referral Center." Endoscopy International Open 6.1 (2018): E98-E103, 6 pages.

* cited by examiner

*Primary Examiner* — Nicholas W Woodall
(74) *Attorney, Agent, or Firm* — Bookoff McAndrews, PLLC

(57) ABSTRACT

Systems and methods for treating tissue may include one or more delivery devices, a grasping element, a first ring for anchoring to a wall of a gastrointestinal tract, and a second ring operably couplable to a radially inward surface of the first ring. Other embodiments include methods of treating tissues, including tubular tracts of tissue, comprising coupling a first ring to first tissue of a wall of a tissue tract, relocating a target tissue proximally to a position proximal to the first ring, coupling a second ring to the first ring, and cutting tissue proximal to the interface of the first and second rings.

19 Claims, 12 Drawing Sheets

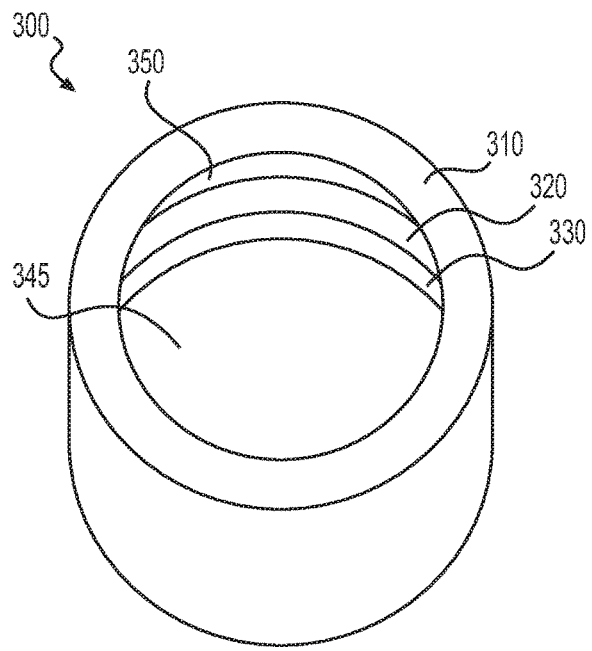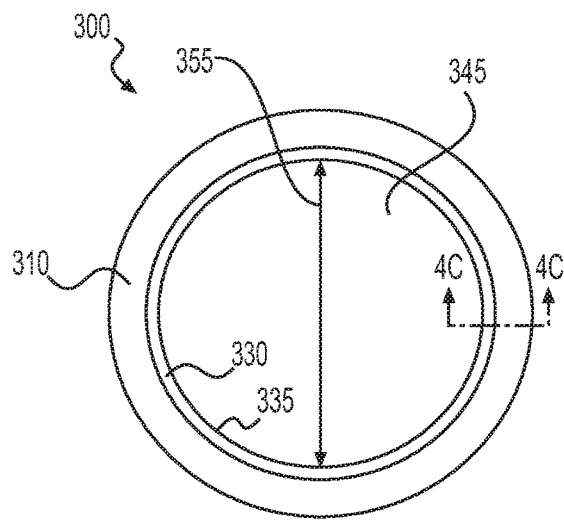
FIG. 4A  FIG. 4B
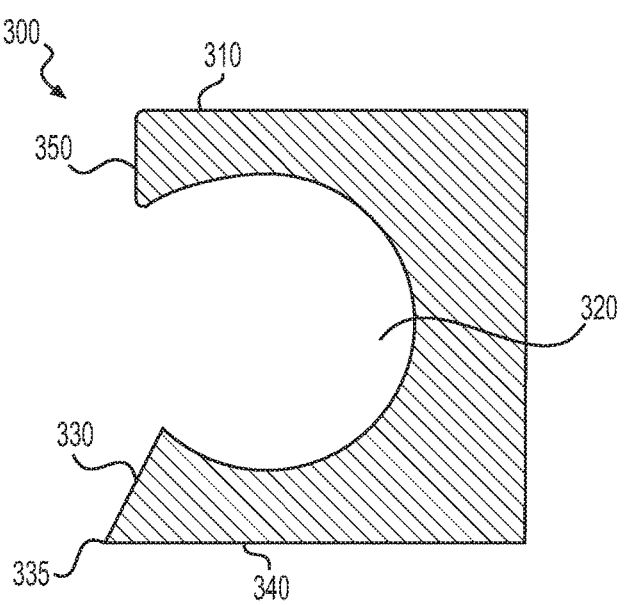
FIG. 4C

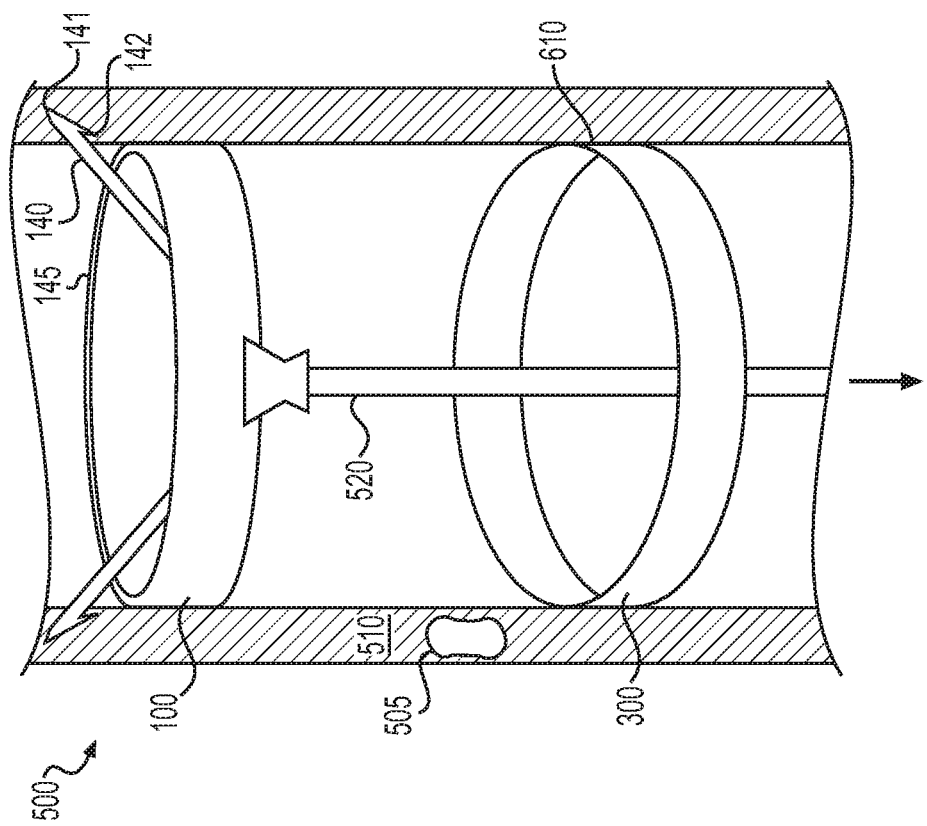
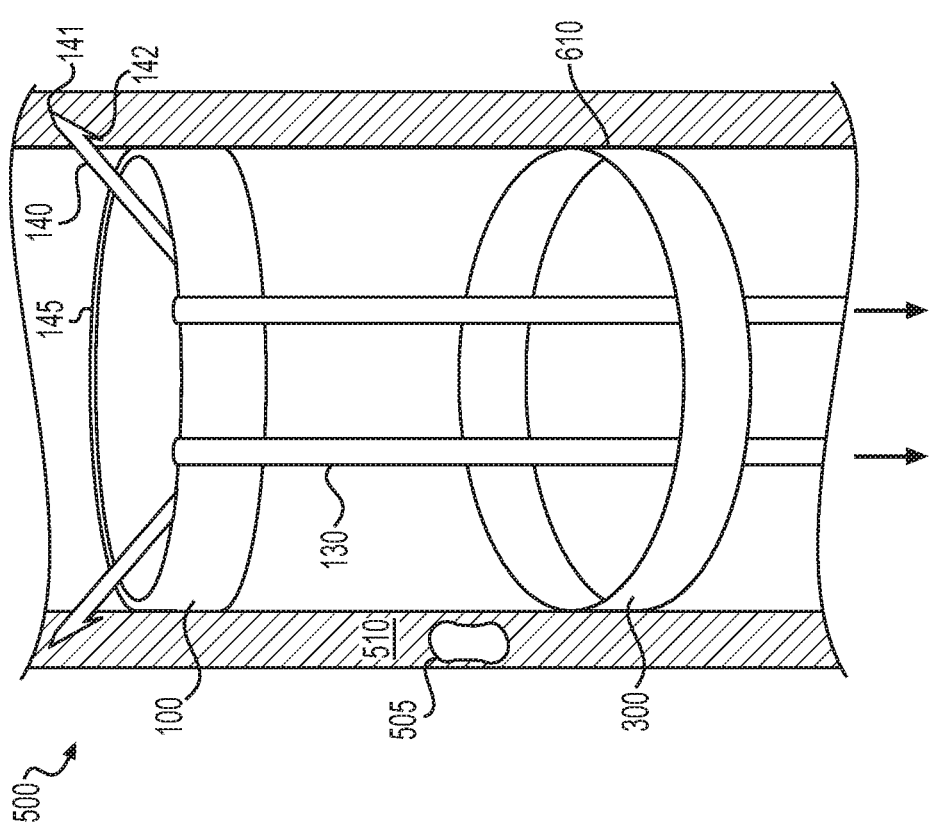

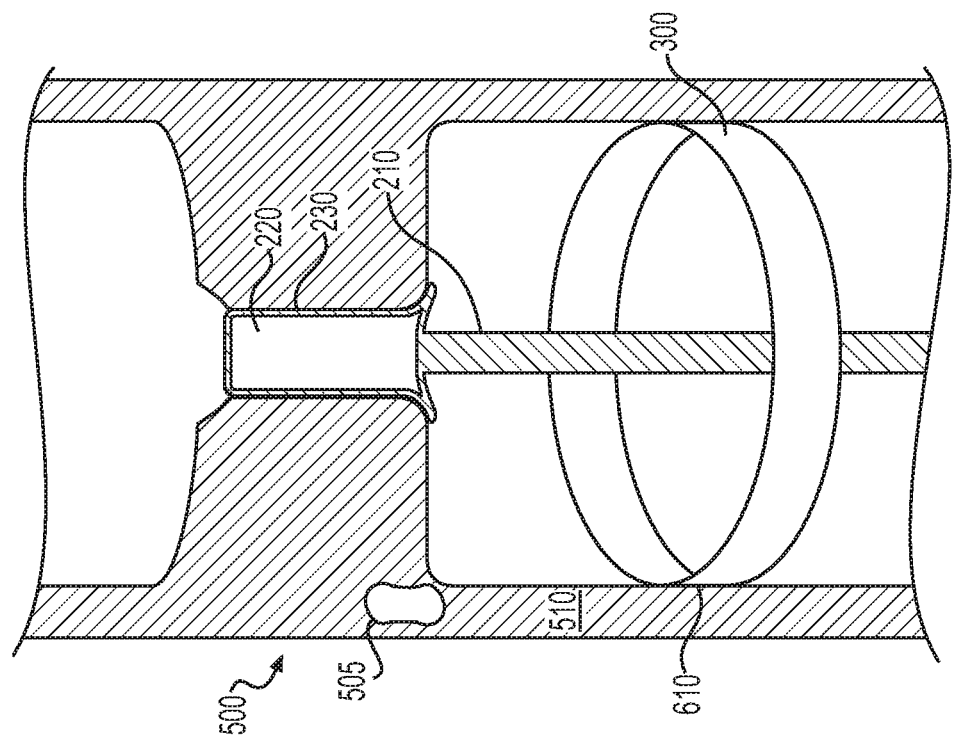
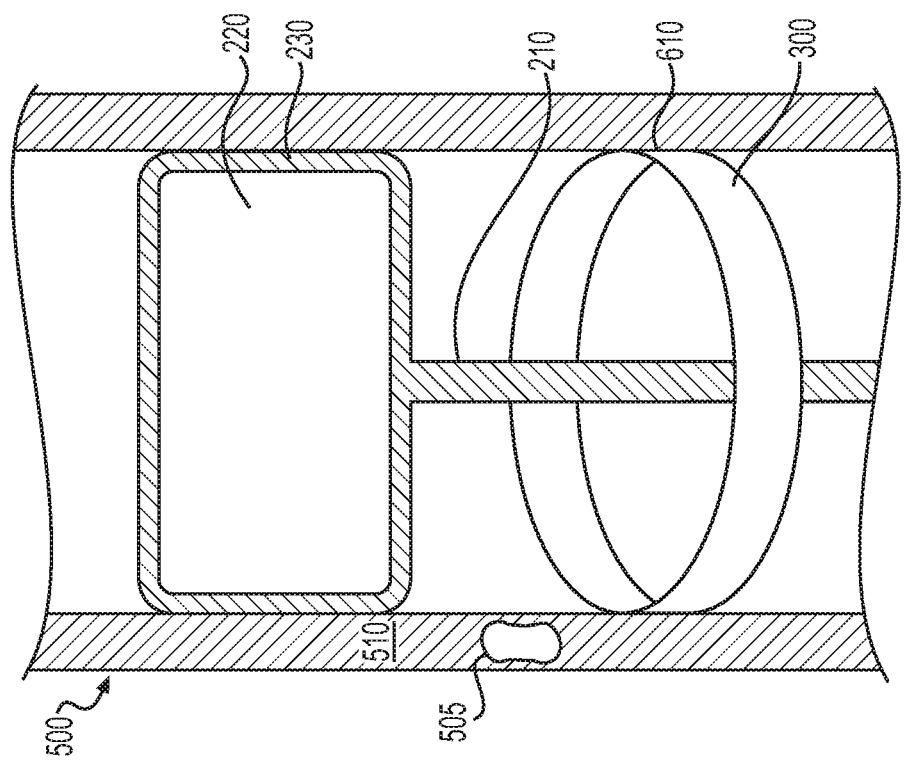

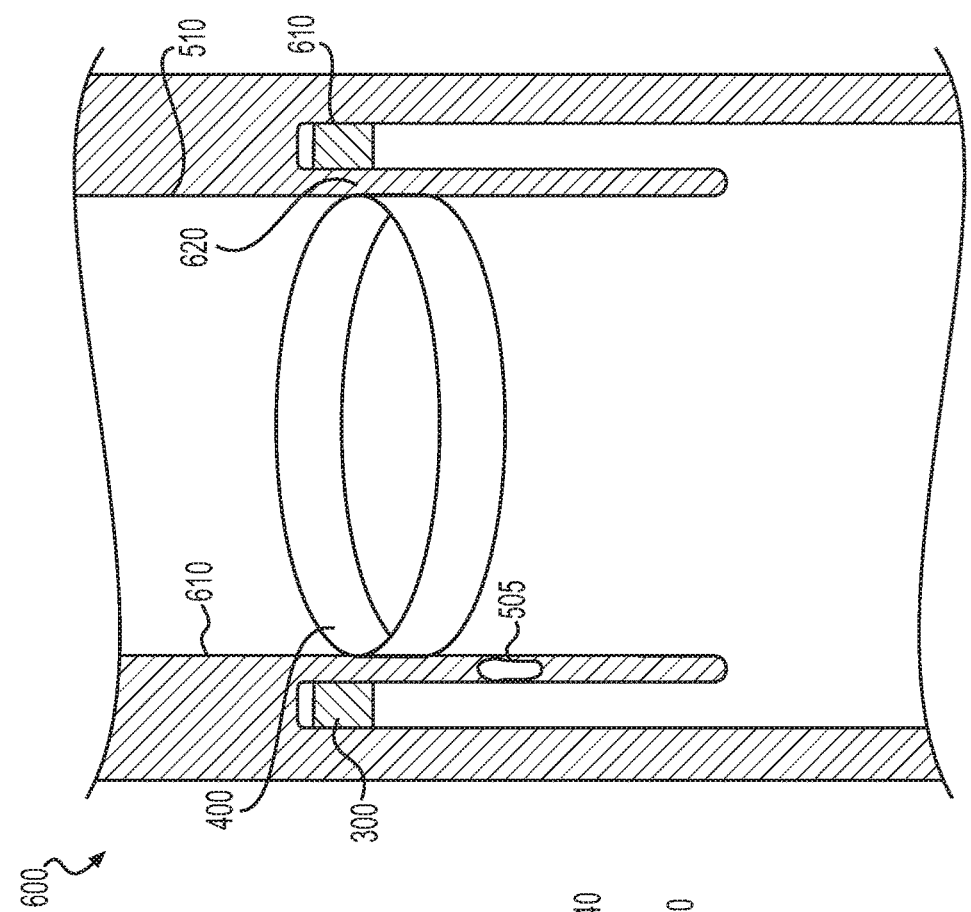
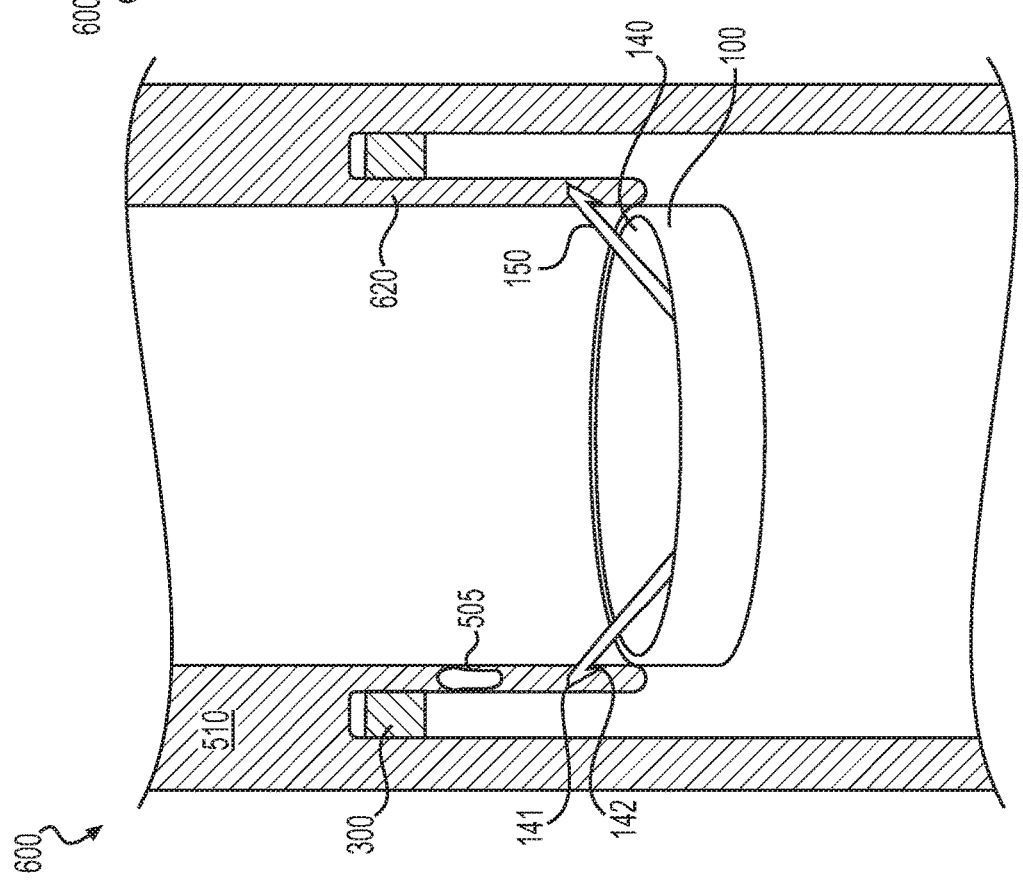
FIG. 11
FIG. 10

SYSTEMS AND RELATED METHODS FOR TISSUE TREATMENT

CROSS-REFERENCE TO RELATED APPLICATIONS

This application claims the benefit of priority from U.S. Provisional Application No. 62/690,622, filed on Jun. 27, 2018, which is incorporated by reference herein in its entirety.

TECHNICAL FIELD

Embodiments of the present disclosure relate generally to medical instruments. More specifically, embodiments of the present disclosure relate to medical instruments and related methods for treating tissue.

INTRODUCTION

Endoscopes may be used in the diagnosis and/or treatment of a wide range of diseases and disorders that typically require a physician to access and navigate internal anatomical lumens within a subject. In use, an endoscope may be positioned in a desired portion of the subject, and one or more treatment instruments may be advanced through a working channel of the endoscope to the desired portion of the subject.

For example, certain tissue dissection procedures involve cutting tissue from within the lumen of tubular tissue, such as lumens of the gastrointestinal tract. During such dissection procedures, it may be difficult to accurately cut only the desired tissue. These difficulties may arise from lack of visibility and lack of maneuverability of tools and instruments within the lumen of the tubular tissue. Such difficulties during the dissection procedures can lead to the perforation of underlying tissues and may otherwise deleteriously affect a subject.

Some harmful growths, such as, for example invasive cancers including T1 and T2 lesions are difficult to resect using conventional endoscopic tools and techniques. These growths may grow or expand through multiple layers of tissue, while current endoscopic tools and methods may be limited to resections in the submucosal layers. One option is to perform a full-thickness resection of the target tissue (e.g., tissue comprising the deleterious growth). However, full-thickness resections are not generally used with endoscopic tools and methods considering the difficulties visualizing adjacent anatomy during endoscopic procedures.

Dissections involving tubular tissue, such as tissue of a gastrointestinal tract, may be particularly problematic because the integrity of the tubular tissue is an important part of the dissection procedure. The lumen of tubular tissue often contains fluids and other matter than need to be retained within the lumen. Perforation of the tubular tissue or other maleffect from a difficult procedure may compromise the ability of the tissue to retain fluids or other matter within the lumen. Post-procedure leaking of these fluids and matters from the lumen into adjacent anatomy may be harmful or even deadly to the subject.

SUMMARY

In one aspect, the present disclosure is directed to a system for treating tissue. The system may have one or more delivery devices, a grasping element, a first ring for anchoring to a wall of a gastrointestinal tract, and a second ring operably coupleable to a radially inward surface of the first ring. The second ring may include one or more cutting mechanisms. In one embodiment, the one or more cutting mechanisms are operable to cut tissue when the second ring is coupled to the radially inward surface of the first ring. In one aspect, the second ring mechanically interlocks with the radially inward surface of the first ring.

The system may also include a flexible endoscope. The one or more delivery devices of the system may have a diameter less than or equal to an inner diameter of the first ring, when the first ring is in an expanded state. One or more of the first ring, the second ring, or the grasping element may be deployable by the one or more delivery devices of the system. In one aspect, the first ring, the second ring, the tissue grasping element, or combinations thereof may be tethered to the one or more delivery devices. In other aspects, one or more of the first ring, the second ring, or the grasping element may include a radially expandable ring. The grasping element may be inflatable. The grasping element may include barbs, spikes, hooks, an adhesive compound, or other means for affixing to tissue. In one embodiment, a grasping element may include barbs that extend radially outward from the grasping element when the grasping element is in an expanded state. The first ring, the second ring, or both may include a bioabsorbable material. The second ring, when coupled to a radially inward surface of the first ring, may be able to rotate about a luminal axis relative to the first ring. In addition, the first and second rings may be configured such that, when coupled together, a fluidic seal is formed between the first and second rings.

In another aspect, the present disclosure is directed to a method of treating tissue. The method may include coupling a first ring to first tissue of a wall of a gastrointestinal tract, proximal to a target tissue, relocating the target tissue proximally to a position proximal to the first ring so that second tissue overlies the first ring, coupling a second ring to the first ring, with the second tissue between the first ring and the second ring, and cutting tissue proximal to the second tissue.

The method may further include inserting an endoscope into the gastrointestinal tract. Additionally or in the alternative, the method may further include deploying a grasping element to the wall of the gastrointestinal tract, distal to the target tissue. The grasping element may include barbs, spikes, hooks, or other means for affixing to tissue. The step of relocating the target tissue may include relocating the grasping element from a position distal to the target tissue to a position proximal to the first ring. The coupling of the second ring to the first ring may cut tissue. In one or more embodiments, the tissue cut by the coupling of the second ring to the first ring may be proximal to the second tissue. In at least one embodiment, the cutting tissue proximal to the second tissue comprises a full thickness resection. The coupling of the second ring to the first ring may form a fluidic seal along the wall of the gastrointestinal tract. The first ring, the second ring, or both may include a radially expandable ring.

In another aspect, the preset disclosure is related to a method of treating tissue. The method may include coupling a grasping element to first tissue of a wall of a gastrointestinal tract, distal to a target tissue, coupling a ring to the wall of the gastrointestinal tract, proximal to the first tissue, relocating the first tissue to a location proximal to a second tissue, the target tissue being located between the first tissue and the second tissue, and coupling a second ring to the first ring, with tissue of the wall of the gastrointestinal tract between the first ring and the second ring.

The method may further include cutting tissue between the second tissue and the target tissue. The cutting tissue may include a full thickness resection. Alternatively or in addition, the method may include the removal of the target tissue from the gastrointestinal tract. The coupling of the second ring to the first ring forms a fluidic seal along the wall of the gastrointestinal tract.

In yet another aspect, the present disclose relates to a method of treating tissue. The method may include coupling a grasping element to a first section of a wall of a tubular tissue, relocating the grasping element proximally, thereby inverting a length of the tubular tissue such that the first section overlies a second section of the wall, and cutting the wall of the tubular tissue distal to the first section.

The method may further include placing a first ring such that, after the length of the tubular tissue is inverted, the first ring lies between the inverted length and the second section of the wall. The method may further include placing a second ring distal to the first section of the interior wall. Alternatively or in addition, the method may further include coupling the first ring to the second ring, whereby the coupling the first ring to the second ring cuts the wall of the tubular tissue distal to the first section. The cutting may include a full-thickness resection.

BRIEF DESCRIPTION OF THE DRAWINGS

Embodiments of the present disclosure may be implemented in connection with aspects illustrated in the attached drawings. These drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

For simplicity and clarity of illustration, the figures depict the general structure and/or manner of construction of the various embodiments described herein. For ease of illustration, the figures may depict various components as uniform and smooth shapes. However, a person skilled in the art would recognize that, in reality, the different components may have a non-uniform thickness and/or irregular shapes. Descriptions and details of well-known features (e.g., delivery mechanisms, catheters, scopes, etc.) and techniques may be omitted to avoid obscuring other features. Elements in the figures are not necessarily drawn to scale. The dimensions of some features may be exaggerated relative to other features to improve understanding of the exemplary embodiments. Cross-sectional views are simplifications provided to help illustrate the relative positioning of various regions/layers and describe various processing steps. One skilled in the art would appreciate that the cross-sectional views are not drawn to scale and should not be viewed as representing proportional relationships between different regions/layers. Moreover, while certain regions/layers and features are illustrated with straight 90-degree edges, in actuality or practice such regions/layers may be more "rounded" and gradually sloping.

Further, one skilled in the art would understand that, even if it is not specifically mentioned, aspects described with reference to one embodiment may also be applicable to, and may be used with, other embodiments. Moreover, there are many embodiments described and illustrated herein. The present disclosure is neither limited to any single aspect nor embodiment thereof, nor to any combinations and/or permutations of such aspects and/or embodiments. Moreover, each aspect of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate that the embodiment(s) is/are "example" embodiment(s). Further, even though the figures and this written disclosure appear to describe the disclosed systems and methods in a particular order or orientation (e.g. top or bottom), it is understood that elements of the described systems and methods may be combined in any order or in any orientation.

Figure 1A:
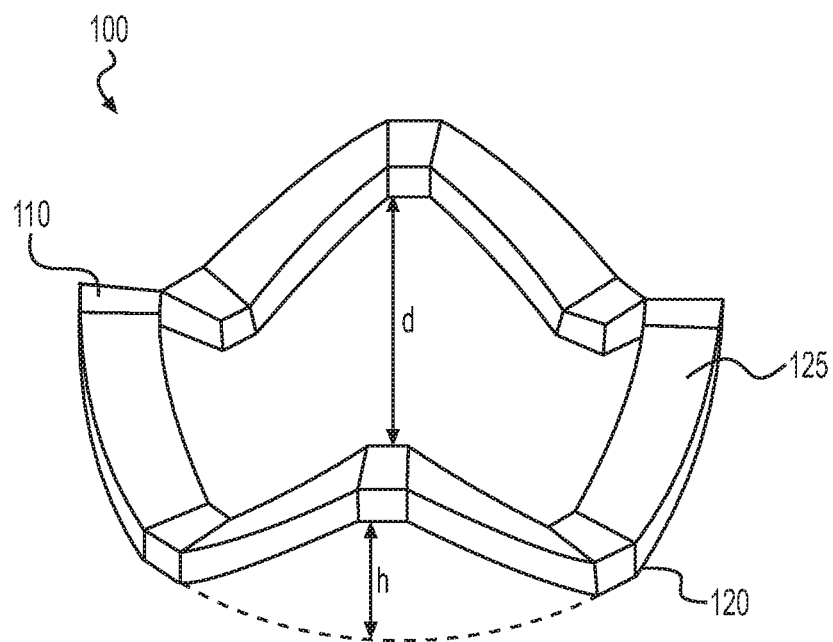
Figure 1B:
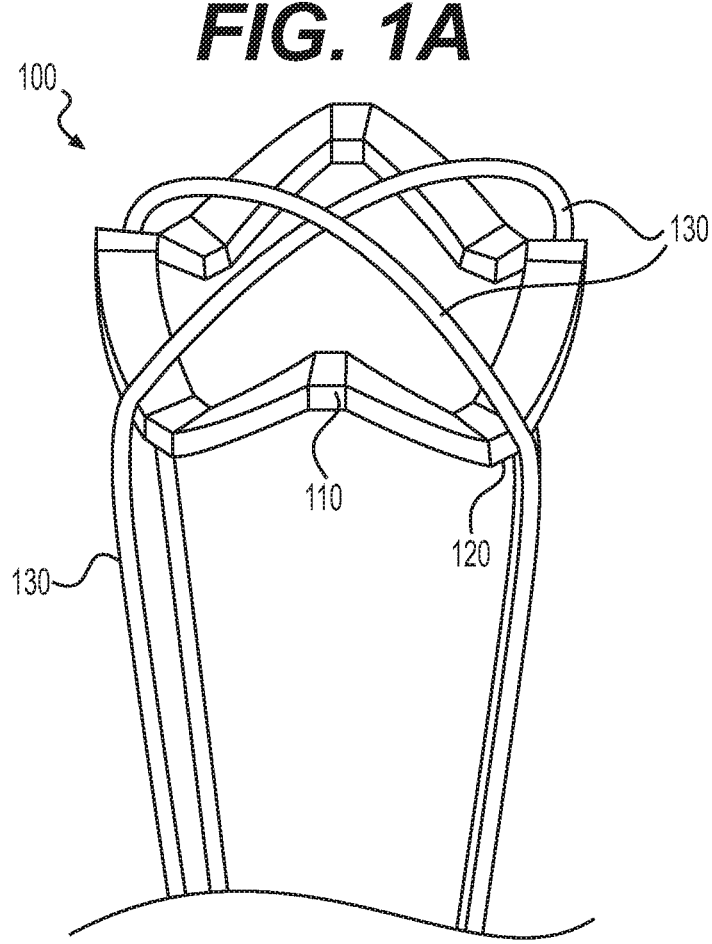

FIGS. 1A-1B illustrate perspective views depicting various exemplary grasping elements, according to one or more embodiments of the present disclosure.

Figure 2A:
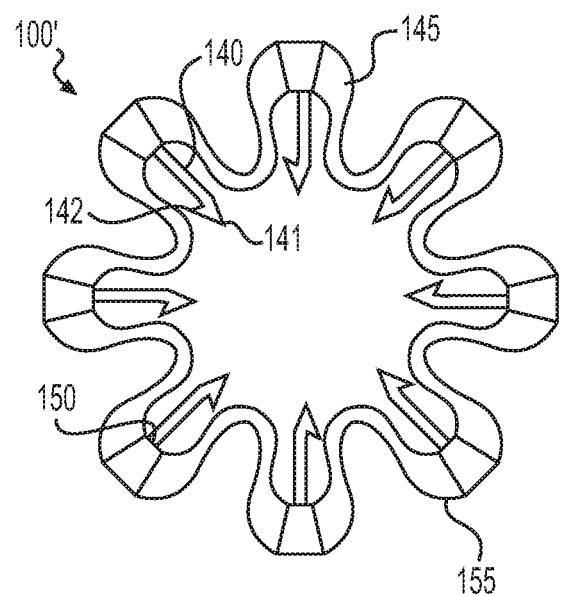

FIG. 2A illustrates a top-down view depicting an exemplary grasping element in a contracted state, according to one or more embodiments of the present disclosure.

Figure 2B:
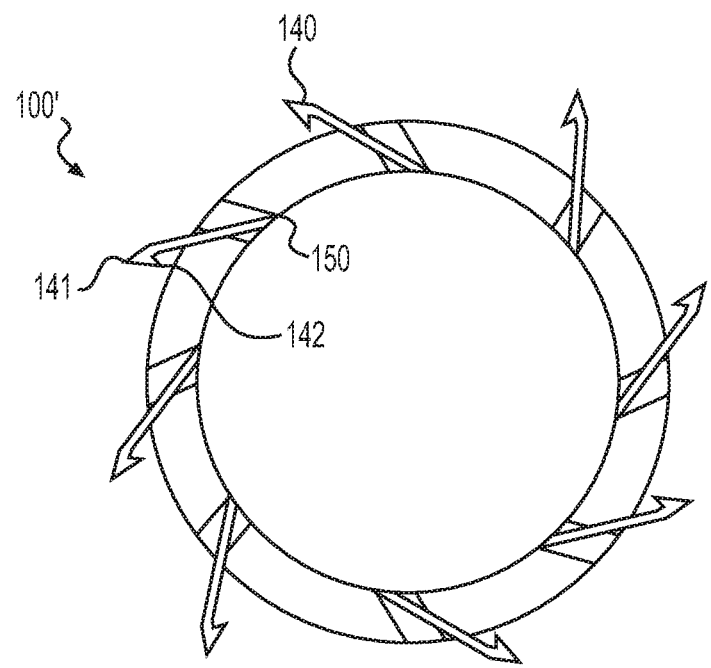

FIG. 2B illustrates a top-down view of the grasping element shown in FIG. 2A, in an expanded state.

Figure 3A:
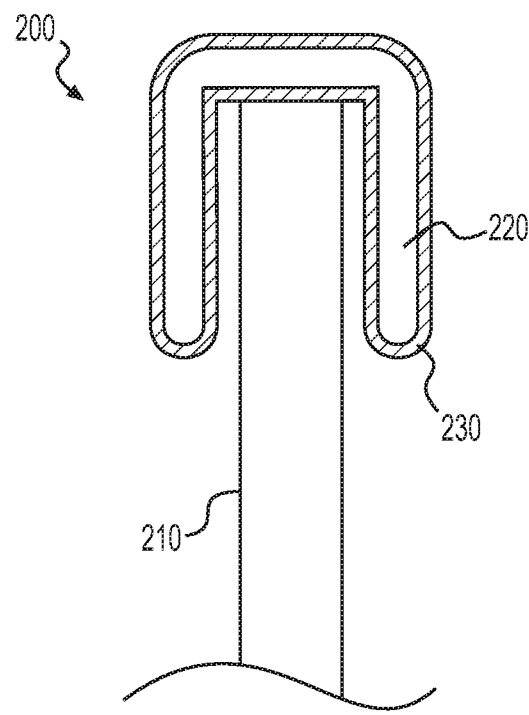

FIG. 3A illustrates a cross-sectional view depicting an exemplary inflatable grasping element in a contracted state, according to one or more embodiments of the present disclosure.

Figure 3B:
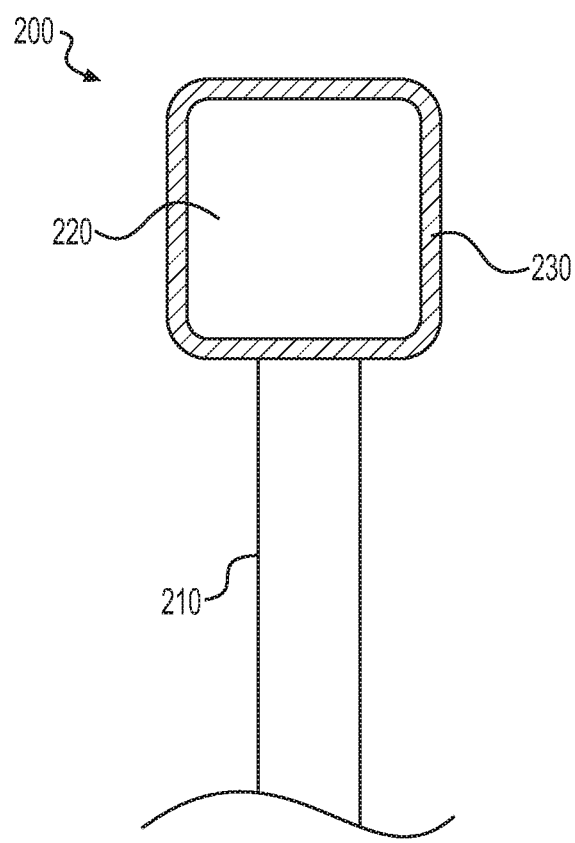

FIG. 3B illustrates a cross-sectional view depicting the inflatable grasping element shown in FIG. 3A, in an expanded state.

FIG. 4A illustrates a perspective view depicting an anchor ring, according to one or more embodiments of the present disclosure.

FIG. 4B illustrates a top-down view depicting the anchor ring shown in FIG. 4A.

FIG. 4C illustrates a cross-sectional view depicting the anchor ring shown in FIGS. 4A-4B, along line 4C-4C of FIG. 4B.

Figure 5A:
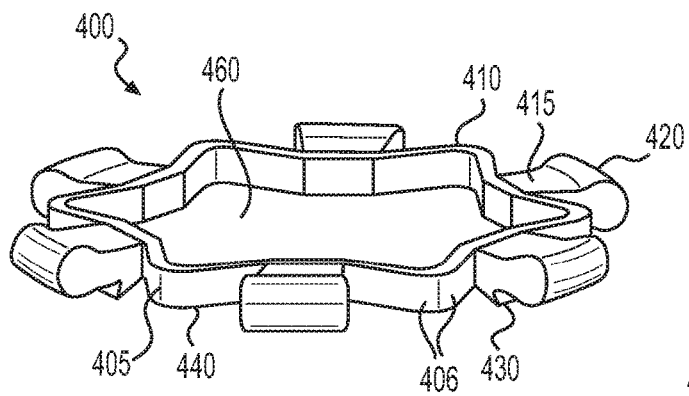

FIG. 5A illustrates a perspective view depicting an excision ring, according to one or more embodiments of the present disclosure.

Figure 5B:
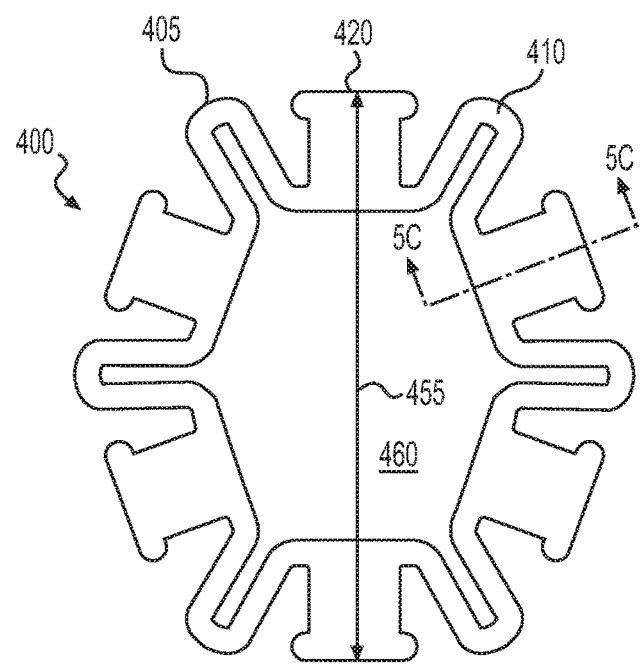

FIG. 5B illustrates a top-down view depicting the excision ring shown in FIG. 5A.

Figure 5C:
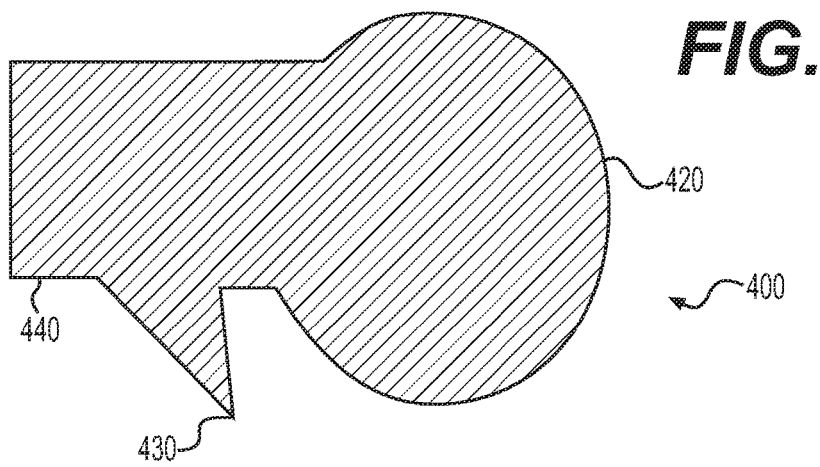

FIG. 5C illustrates a cross-sectional view depicting the excision ring shown in FIGS. 5A-5B, along line 5C-5C of FIG. 5B.

Figure 6:
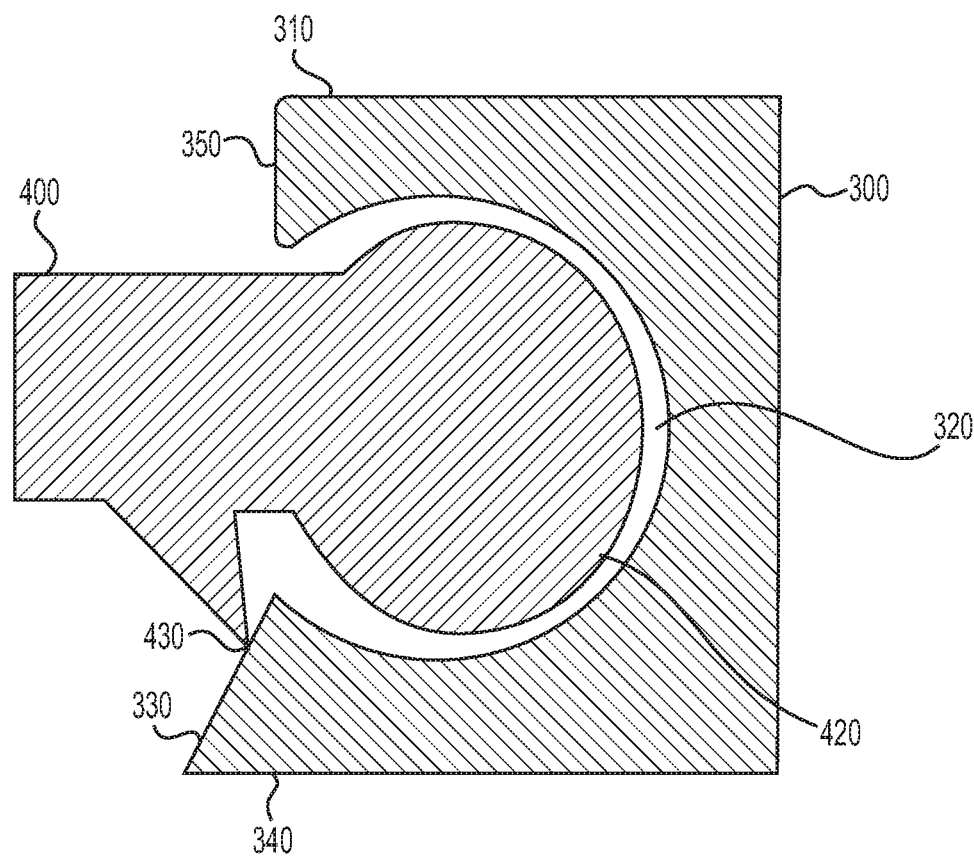

FIG. 6 illustrates a cross-sectional view depicting an exemplary interlocking mechanism between the anchor ring and the excision ring, according to one or more embodiments of the present disclosure.

Figure 7:
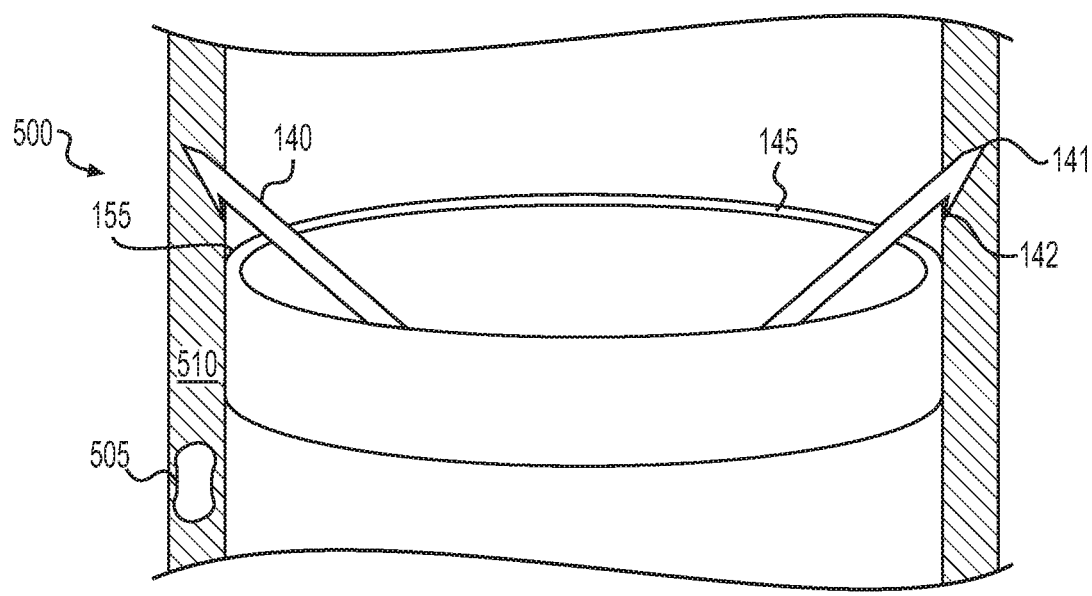

FIG. 7 illustrates a cross-sectional view depicting a grasping element, in an expanded state, affixed to a wall of a gastrointestinal tract, according to one or more embodiments of the present disclosure.

FIGS. 8A-8B illustrate a grasping element affixed to a wall of a gastrointestinal tract distal to an anchor ring, according to one or more embodiments of the present disclosure.

FIG. 9A illustrates a grasping element, in an expanded state, affixed to a wall of a gastrointestinal tract, according to one or more embodiments of the present disclosure.

FIG. 9B illustrates the grasping element affixed to the wall of the gastrointestinal tract shown in FIG. 9A, in a contracted state.

FIG. 10 illustrates a grasping element affixed to a wall of a partially inverted gastrointestinal tract proximal to an anchor ring, according to one or more embodiments of the present disclosure.

FIG. 11 illustrates an anchor ring and an excision ring affixed to the wall of a partially inverted gastrointestinal tract, according to one or more embodiments of the present disclosure.

Figure 12:
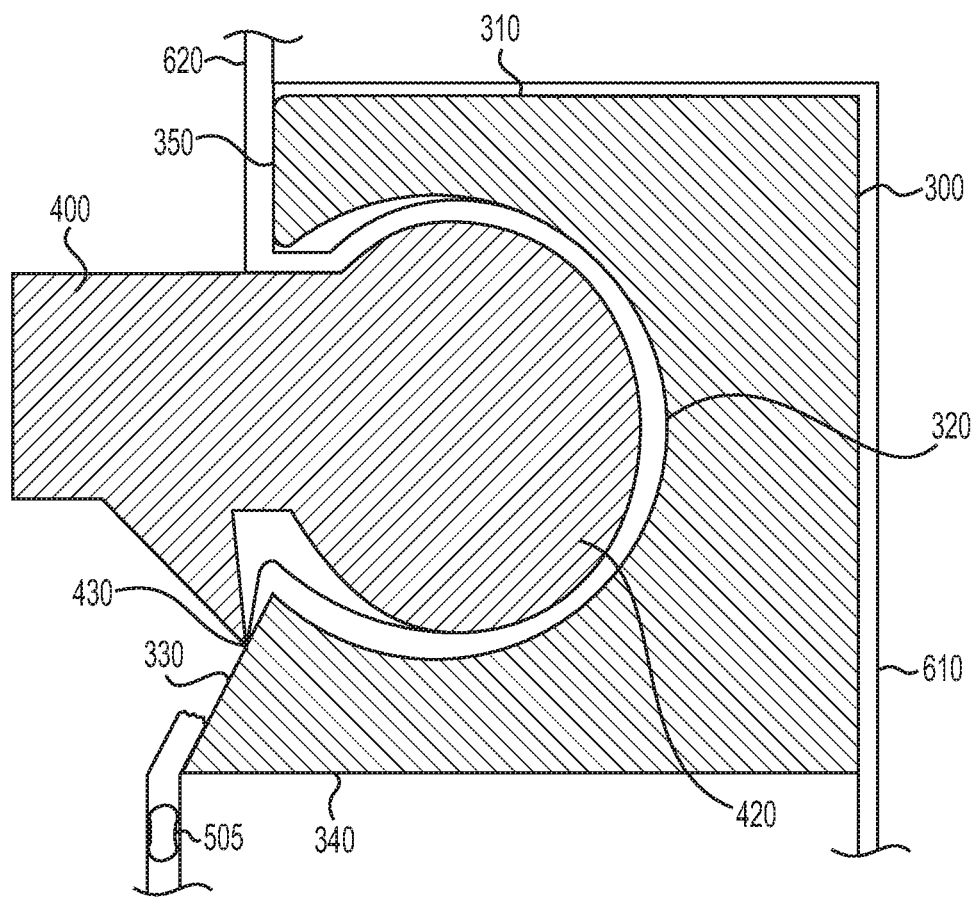

FIG. 12 illustrates a cross-sectional view depicting an anchor ring coupled to an excision ring with tissue between the rings, according to one or more embodiments of the present disclosure.

Figure 13:
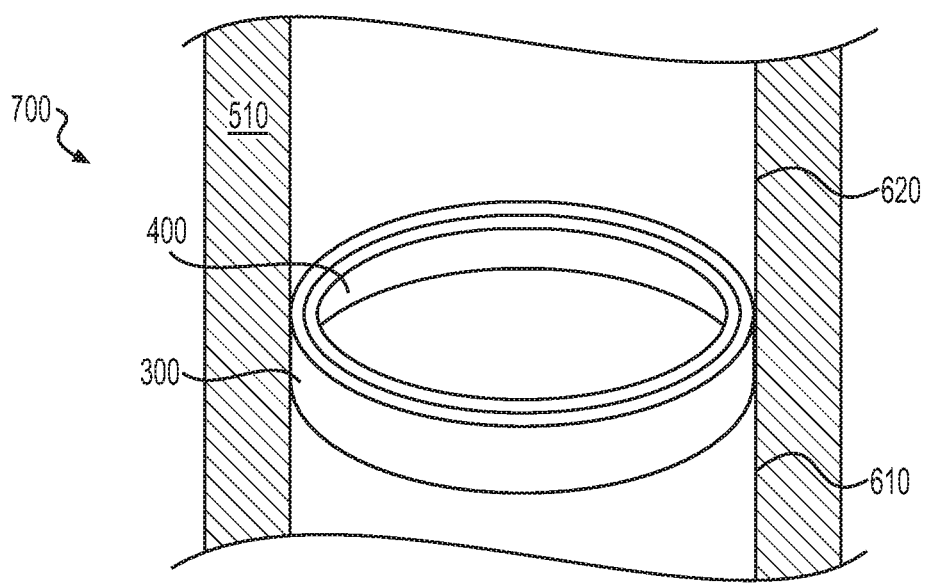

FIG. 13 illustrates a gastrointestinal tract after a full-thickness resection has been performed, according to one or more embodiments of the present disclosure.

Figure 14:
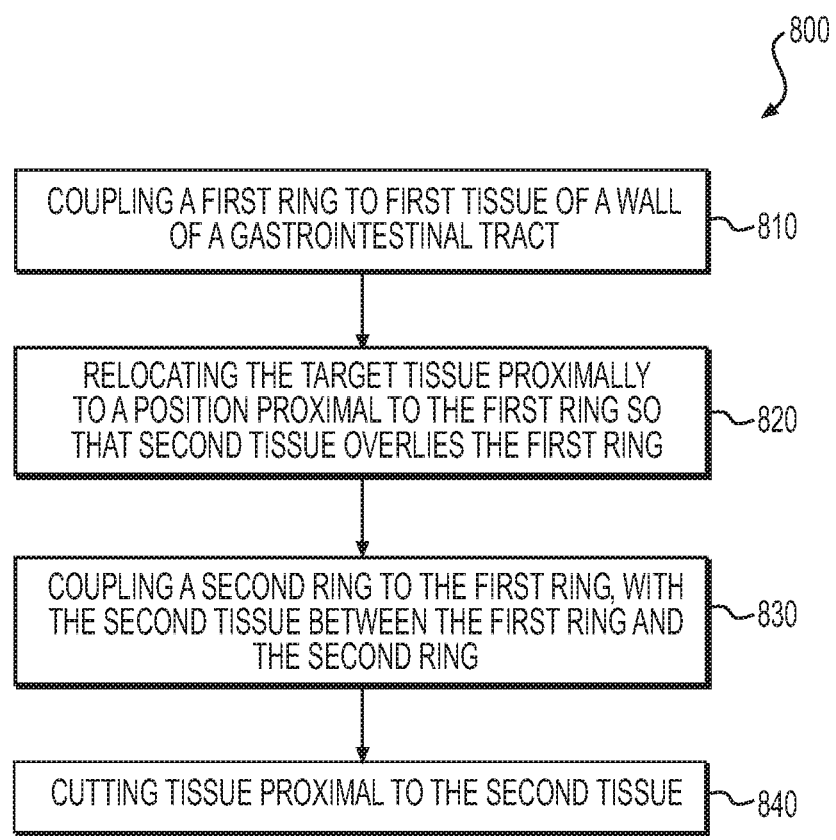

FIG. 14 is a flowchart of a method according to an embodiment of the present disclosure.

Figure 15:
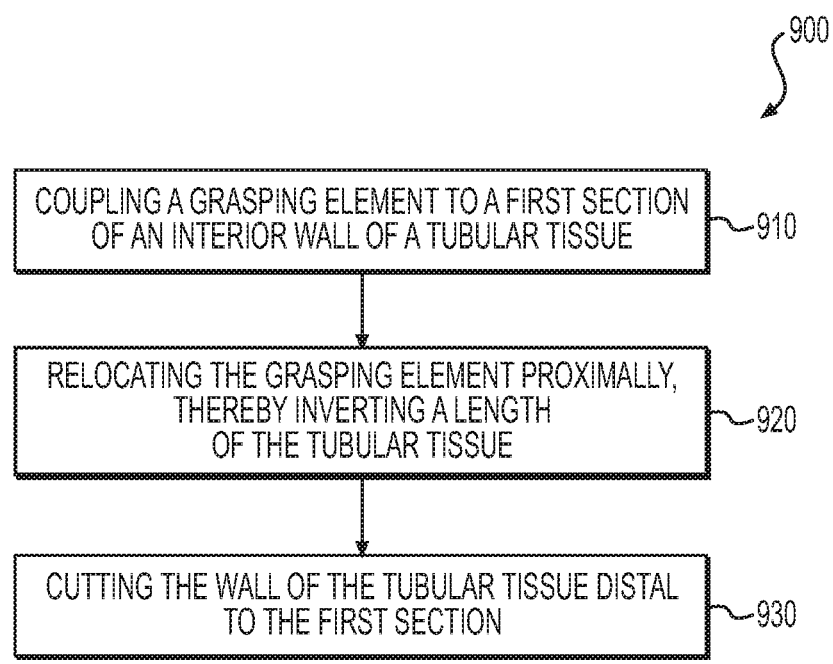

FIG. 15 is a flowchart of a method according to another embodiment of the present disclosure.

Again, there are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

It should be noted that the description set forth herein is merely illustrative in nature and is not intended to limit the embodiments of the subject matter, or the application and uses of such embodiments. Any implementation described herein as exemplary is not to be construed as preferred or advantageous over other implementations. Rather, the term "exemplary" is used in the sense of example or "illustrative," rather than "ideal." The terms "comprise," "include," "have," "with," and any variations thereof are used synonymously to denote or describe a non-exclusive inclusion. As such, a device or a method that uses such terms does not include only those elements or steps, but may include other elements and steps not expressly listed or inherent to such device and method. Further, the terms "first," "second," and the like, herein do not denote any order, quantity, or importance, but rather are used to distinguish one element from another. Similarly, terms of relative orientation, such as "top," "bottom," etc. are used with reference to the orientation of the structure illustrated in the figures being described. The term "distal" refers to the direction that is away from the user or operator and into the subject. By contrast, the term "proximal" refers to the direction that is closer to the user or operator and away from the subject. Moreover, the terms "a" and "an" herein do not denote a limitation of quantity, but rather denote the presence of at least one of the referenced item.

Embodiments of the present disclosure are directed to systems and methods designed to optionally be used with a flexible endoscopic device, having one or more lumens therein. Components of the system described herein or elements of the methods detailed herein may be configured to extend through an such endoscopic device. Endoscopes that are compatible with the systems and methods described herein may be used for procedures within or adjacent to various organs such as an esophagus, circulatory pathway or hub, a stomach, a bladder, an intestine, a colon, or any other portion of a subject including the gastrointestinal, urinary, or pulmonary tracts. Such endoscopes may include a proximal end, a distal end, and one or more channels extending from the proximal end to the distal end. One or more delivery devices, as described below, may be disposed within the one or more channels. Additionally, the proximal end may include one or more control mechanisms for operating or controlling the scope, the distal end of the scope, the one or more channels, one or more or delivery devices, one or more associated other devices, or a combination thereof.

In embodiments of the present disclosure, a system for treating tissue comprises one or more delivery devices, a grasping element, a first ring, and a second ring. The treatment may include removal of a target tissue. The one or more delivery devices may be used to deliver the grasping element, first ring, and second ring. The first ring may be delivered to a tubular tissue (e.g. gastrointestinal tract) and affixed to a surface of the wall of the tract. The grasping element may be used to move the target tissue from a position distal to the first ring to a position proximal to the first ring. The second ring may be operably coupleable to a radially inward surface of the first ring. In some embodiments, the tissue may be cut such that the target tissue is excised from the remaining tissue.

In embodiments of the present disclosure, one or more delivery devices may comprise a delivery catheter, or other elongate tubular member having an internal lumen. One or more grasping elements, rings, or other devices may be disposed within the lumen of the delivery catheter. Other suitable deliver devices include sheaths, colonoscopes, duodenoscopes, endoscopes, or the like. Any of the previously described delivery devices may be used to dispose grasping elements, anchor rings, excision rings, or combinations thereof, within a tract of tissue, according to one or more embodiments of the present disclosure.

Referring to FIG. 1, a grasping element 100 may be ring-shaped with a series of distal ridges 110, each alternating with one of a series of proximal ridges 120, about a circumference of grasping element 100. The three-dimensional space between proximal ridges 120 and a distal ridge 110 allows for tissue to sink in around the edges of grasping element 100. Tissue sinking in around the edges of grasping element 100 creates a larger surface area of interaction between tissue and grasping element 100. Without being limited by theory, it is believed the force affixing grasping element 100 to the tissue increases as the surface area of interaction between tissue and grasping element 100 increases. The grasping element 100 may be radio-opaque and may comprise any suitable material, such as, for example, a metal, a metal alloy, a metalloid, or a polymer (e.g., a bioabsorbable polymer). In one or more embodiments, grasping element 100 may comprise an alloy including nickel and titanium (e.g., nitinol) or other alloy exhibiting shape memory effect, pseudoelasticity, or both.

Accordingly, grasping element 100 may exist in a collapsed state or an expanded state. As used in the context of grasping element 100, a diameter, d, is defined as the largest straight line that can be drawn from one distal ridge 110 to the opposing distal ridge 110 across a center point of grasping element 100. Similarly, in the context of grasping element 100, a height, h, is defined as the vertical displacement from a distal ridge 110 to a neighboring proximal ridge 120. In transitioning (e.g. reverting) from a collapsed state to an expanded state, grasping element 100 increases in diameter and decreases in height. In transitioning from an expanded state to a collapsed state, grasping element 100 decreases in diameter and increases in height. In at least one embodiment, the grasping element in an expanded state has a non-zero height (e.g., there is vertical displacement between neighboring distal ridges 110 and proximal ridges 120.

In one or more exemplary embodiments, grasping element 100 comprises four distal ridges 110 and four proximal ridges 120, equally spaced in an alternating placement around a circumference of grasping element 100, as shown in FIG. 1A. In other embodiments, grasping element 100 may comprise two or more distal ridges 110, such as, for example, two, four, six, or eight distal ridges 100. Grasping element 100 may comprise two or more proximal ridges 120, such as for example, two, four, six, or eight proximal ridges 120. There also may be an odd number of one or both of distal ridges 110 and proximal ridges 120. The proximal ridges 120 may alternate with the distal ridges 110 around a circumference of grasping element 100, forming an undulating ring, as shown in FIG. 1A. Body segments 125 connect neighboring proximal ridges 120 and distal ridges 110, completing the ring shape of grasping element 100.

In embodiments including a grasping element 100 comprising an alloy including nickel and titanium or other alloy exhibiting shape memory effect or pseudoelasticity, the shape memory effect or pseudoelasticity of the grasping element 100 allow it to revert between collapsed and expanded states. The grasping element 100 may be in a collapsed state while disposed in a delivery device and may revert to an expanded state after exiting the delivery device. In other embodiments, grasping element 100 may be in an expanded state while disposed in the delivery device and delivered therefrom. Alternatively, grasping element 100 may be triggered to revert to an expanded state upon some trigger other than the exiting of the delivery device. Additionally, in an expanded state, the elasticity or pseudoelasticity of the grasping element 100 allows for a greater force to be exerted on the tissue by the grasping element 100, increasing the force affixing the grasping element 100 to the tissue.

In one or more embodiments, such as those depicted in FIG. 1B, one or more tethers 130 may be used to assist in deployment and retrieval of grasping element 100. The tethers 130 may extend from a proximal ridge 120 of grasping element 100, and loop around the grasping element 100 returning back to the proximal end of the delivery device. Tethers 130 may function to keep grasping element 100 in communication with a delivery device, endoscope, or other control or delivery mechanism. The tethers 130 may operably be extended or retracted depending on the desired placement or positioning of the grasping element 100.

As shown in FIG. 1B, one embodiment comprises two tethers 130 intersecting perpendicularly (or approximately perpendicularly) distal to grasping element 100. Each tether 130 extends from a delivery device (not pictured) to a proximal ridge 120, distally over grasping element 100 to the opposing proximal ridge 120, and then back to the delivery device. In other embodiments, only one tether 130 may be connected to grasping element 100, while in still other embodiments, three or more tethers 130 may be connected to grasping element 100. In embodiments comprising a plurality of tethers 130, the tethers 130 may be connected to one delivery device or a plurality of delivery devices. The tethers 130 may be drawn or pulled proximally by the connected one or more delivery devices or other operating means. After grasping element 100 expands in a tissue tract and tissue sinks in over the proximal ridges 120 and distal ridges 100, the tissue around grasping element 100 may be relocated by drawing in or applying another proximal force on the tethers 130. The pressure of the radially expanding grasping element 100 against the tissue and the friction between the tissue and grasping element 100 maintains contact between the grasping element 100 and tissue even when a force is applied to the tethers 130. In some embodiments, this may cause the tissue to move with the tethers 130 and grasping element 100 when a proximal force is applied to the tethers 130 via delivery device or other operating means.

The tethers 130 may comprise flexible materials such as metals, alloys, or flexible polymeric materials. The tethers 130 may be shaped as wires, cables, threads, or other flexible structures capable of extending from a delivery device and distally around opposing proximal ridges 120.

In some embodiments, such as those depicted in FIGS. 2A-B, the grasping element may comprise barbs, spikes, hooks, an adhesive, or means for affixing to tissue other than an expansion or tensioning force. In one or more embodiments, the barbs, spikes, hooks, or other means extend radially from the grasping element. By way of example, and not limitation, one such grasping element 100' is depicted in FIGS. 2A-B.

Referring to FIG. 2A, in one embodiment, a grasping element 100' comprises one or more barbs 140 extending from one or more barb joints 150, the one or more barb joints 150 being spaced around the grasping element body 145. A barb joint 150 is a surface, and the adjacent region, that forms an interface between the grasping element body 145 and a barb 140. Each barb may comprise a sharp tip 141 and an anchor 142. The sharp tip 141 is able to pierce tissue, and the anchor 142 prevents the barb from slipping or being pulled out of the tissue. While the grasping element 100' is in a collapsed state, as depicted in FIG. 2A, one or more barbs 140 are directed radially inward, away from the radially exterior edge 155 of the grasping element 100'. In one or more embodiments, grasping element 100' may further comprise proximal ridges 120, distal ridges 110, and body segments 125 to form an undulating grasping element 100', as previously described. One or more barb joints 150 may be located at or near one or more proximal ridges 120 or distal ridges 110. In some embodiments, tethers 130 connect a grasping element 100' to a delivery device, as previously described.

When the grasping element 100' reverts to an expanded state, as depicted in FIG. 2B, the barb joints 150 rotate with respect to the surrounding grasping element body 145 to extend one or more barbs 140 outward, past radially exterior edge 155 of grasping element 100'. When grasping element 100' is deployed in a tract of tissue and transitions to an expanded state, the barbs 140 may pierce the tissue. However, grasping element 100' may be configured so that the barbs 140 do not extend so far past the exterior edge 155 of the grasping element 100 as to perforate (e.g., puncture through the entire thickness of) the tissue. Those skilled in the art would appreciate that depending on the intended placement within the subject, the surrounding tissue may vary in thickness such that various grasping elements 100' may be configured to extend barbs 140 a variety of distances radially past the exterior edge 155 of the grasping element 100' as to fit the desired application.

In one or more embodiments, the grasping element 100 may be inflatable. Referring to FIG. 3A, an inflatable grasping element 200 may include an inner space 220 defined by an outer wall 230. Outer wall 230 may include any material sufficient to adhere a radially exterior surface of outer wall 30 to tissue. For example, wall 230, and/or an exterior surface of outer wall 230 may comprise fibrin glue, TissueGlu, cyanoacrylate, or other biologically compatible tackifier. Additionally, or in the alternative, the exterior surface of outer wall 230 may be textured or otherwise constructed to frictionally engage a tissue surface. Air, inert gas, saline solution, or other fluid may be transported via a delivery device 210 to the space 220. The space 220 may expand in volume in response to the receipt of such fluid via the delivery device 210.

While in a collapsed state, as depicted in FIG. 3A, the inflatable grasping element 200 may occupy such a volume as to not contact the walls of a tissue tract. As described previously, depending on the intended application, those skilled in the art would appreciate that the tissue surrounding the region of intended application varies and that a variety of sizes and volumes of inflatable grasping elements 200 are contemplated. When transitioning to an expanded state, as depicted in FIG. 3B, via the introduction of air, inert gas, or other fluid, the inflatable grasping device 200 may occupy a volume as to contact the walls of a tissue tract. Outer wall 230 may then affix the inflatable grasping element 200 to the tissue.

Systems of the present disclosure may comprise an anchor ring. As used in the present disclosure, a ring refers to a structure having a proximal end, a distal end, and a lumen extending from the proximal end to the distal end. In some embodiments, a ring may have a circular profile, or other profile having rotational symmetry about a luminal axis (e.g., an axis in the lumen). An anchor ring may be disposed via a delivery device to a wall of a tissue tract (e.g., gastrointestinal tract). The anchor ring may be affixed to the tissue via mechanical or chemical means, including, but not limited to, tension force. The anchor ring may comprise a self-fixating bioabsorbable hook and loop fastener (e.g., Parietex or other polymer mesh) or other bioabsorbable materials. Anchor rings comprising bioabsorbable materials may increase the force affixing the anchor ring to tissue and may improve the post-procedure healing process.

Referring to FIGS. 4A-C, an anchor ring 300 comprises a distal surface 310, a proximal surface 340, a lumen 345, an interior surface 350, a keying region 320, and a cutting surface 330. The keying region 320 is open to lumen 345 of the anchor ring 300 and is disposed between the distal surface 310 and the proximal surface 340. The cutting surface 330 may be disposed at an angle relative to the luminal axis of the ring. In some embodiments an interior surface 350 is disposed transverse to the cutting surface 330 and parallel to the luminal axis. One or more of the interior surface 350, keying region 320, or cutting surface 330 may interface with a second ring, as described herein. An inner diameter 355 of the anchor ring may be defined as the longest straight line between two points along the edge 335 between the cutting surface 330 and the proximal end 340.

Systems of the present disclosure may further comprise an excision ring. An excision ring may be delivered via a delivery device to a wall of a tissue tract (e.g., gastrointestinal tract). The excision ring may be affixed to the tissue via mechanical or chemical means, including, but not limited to, tension force. The excision ring may comprise a self-fixating bioabsorbable hook and loop fastener (e.g., Parietex or other polymer mesh) or other bioabsorbable materials. Excision rings comprising bioabsorbable materials may increase the force affixing the anchor ring to tissue and may improve the post-procedure healing process. In some embodiments, both a first ring and a second ring (e.g., an anchor ring and an excision ring) may comprise self-fixating bioabsorbable hook and loop fasteners, synergistically improving the effects on the tissue affixing force and post-procedure healing.

Referring to FIGS. 5A-C, an excision ring 400 may comprise a wavy, undulating body 405 having a distal surface 410 and a proximal surface 440, a lumen 460 within body 405 between surfaces 410 and 440, and a series of radial protrusions 415, each having a keying region 420. Body 405 of excision ring 400 may comprise a series of legs 406. One or more legs 106 connect neighboring radial protrusions 415. The legs 106 may be flexible and bend to expand or contract excision ring 400. In some embodiments, each radial protrusion 415 may also comprise a cutting edge 430. Radial protrusions 415 are spaced around body 405 of excision ring 400 and protrude radially outward from body 405. In the embodiment shown in FIG. 5A, six radial protrusions 415 are spaced equally around a circumference of excision ring 400. Other embodiment excision rings may comprise one or more radial protrusions 415 and the radial protrusions may be spaced evenly or unevenly around a circumference of excision ring 400. In some embodiments, a cutting edge 430 is adjacent to, radially inward of, and proximal of, one or more of the keying regions 420. In a collapsed state, as depicted in FIGS. 5A-C the outer diameter 455 of the excision ring 400 is smaller than the inner diameter 355 of the anchor ring. The excision ring 400 may radially expand and transition from the collapsed state to an expanded state. In an expanded state, the outer diameter 455 of the excision ring is larger than the inner diameter 355 of the anchor ring.

In an embodiments, the excision ring may comprise an alloy including nickel and titanium or other alloy exhibiting shape memory effect or pseudoelasticity, the shape memory effect or pseudoelasticity of the excision ring 400 allowing it to revert between collapsed and expanded states. Excision ring 400 may be in a collapsed state while disposed in a delivery device and may revert to an expanded state after exiting the delivery device. In other embodiments, excision ring 400 may be in an expanded state while disposed in the delivery device and delivered therefrom. Alternatively, excision ring 400 may be triggered to revert to an expanded state upon some trigger other than the exiting of the delivery device. Additionally, in an expanded state, the elasticity or pseudoelasticity of excision ring 400 allows for a greater force to be exerted on the tissue by excision ring 400, increasing the force coupling excision ring 400 to anchor ring 300.

In some embodiments, all or just the exterior of excision ring 400 comprises a bioabosorbable material. The bioabsorbable material may extend across the entire exterior of excision ring 400, or may be concentrated to one or more surfaces, such as the body 405, the legs 406, or the radial protrusions 415.

Referring to FIG. 6, the keying region 420, the cutting edges 430, or both of excision ring 400 may interface with a radially inward surface of the anchor ring 300. The radially inward surface of anchoring ring 300 that interfaces with excision ring 400 may comprise the interior surface 350, the keying region 320, the cutting surface 330, or a combination thereof. In some embodiments, when excision ring 400 is in an expanded state, keying region 320 may contact keying region 420. Additionally or in the alternative, cutting edges 430 may contact the cutting surface 330. In one or more embodiments, the flexibility or elasticity (e.g., pseudoelasticity) of excision ring 400 may allow keying region 420 to contract sufficiently to enter keying region 320 of anchor ring 300. The flexibility or elasticity of anchor ring 300 may allow keying region 320 to also expand sufficiently to allow keying region 420 to enter region 320.

When the excision ring 400 is coupled to the anchor ring 300, the excision ring 400 may rotate about a luminal axis, with respect to the anchor ring 300. In one or more embodiments, this may allow the cutting edge 330 to contact a 360° arc along the cutting surface 330. Additionally, the coupling of the anchor ring 300 and the excision ring 400 may form a fluidic seal at the interface of the anchor ring 300 and the excision ring 400. In one embodiment, the fluidic seal exists at the interface where the keying region 420 and keying region 320 are in contact with either side of a wall of tissue. In other embodiments, the fluidic seal may be formed between a wall of tissue and a proximal surface 340 or a distal surface 310 of anchoring ring 300. As used herein, a fluidic seal refers to an interface between structures or components that is impermeable, or substantially not permeable, to fluids.

Reference will now be made to one or more methods using one or more embodiment systems previously described. As previously mentioned, reference will be made to figures which include simplified depictions of elements of systems previously described in order to highlight aspects of the embodiment methods. It should be understood that the descriptions of elements of the systems are applicable to like elements described below in the embodiment methods regardless of the specific physical depictions in the exemplary figures.

According to one or more embodiments, a method may comprise coupling a first ring to first tissue of a wall of a gastrointestinal tract. As described previously, an anchor ring 300 may be disposed in a tract of tissue 500 and may be affixed to a tissue at a surface 610 of a wall 510 of the tract of tissue 500. The anchor ring 300 may be deployed via a delivery catheter or other delivery device and is coupled to a first tissue 610 via chemical or mechanical means (e.g., tension forces), as shown in FIG. 8A.

In one or more embodiments, a method may further comprise relocating a target tissue proximally to a position proximal to the first ring so that second tissue overlies the first ring. Various grasping elements 100, 200 may be employed to relocate a target tissue proximally to a position proximal to the anchor ring 300. For example, referring to FIG. 7, a grasping element 100 may be placed in tissue tract 500, and affixed to a wall 510 of the tissue tract 500. While in an expanded state, the grasping element 100 has barbs 140 that protrude distally past the grasping element body 145 and radially outward past the exterior edge 155. The barbs may pierce the tissue wall 510, without perforating the tissue tract 500. One means of relocating a target tissue 505 proximally to a position proximal to the first ring (e.g., an anchor ring 300) includes placing the grasping element 100 distal to target tissue 505 (as seen in FIGS. 8A-8B). In other embodiments, the grasping element 100 may be placed proximal to the target tissue 505. Referring to FIGS. 8A-B, in one or more embodiments, after an anchor ring 300 is coupled to first tissue at surface 610 and, after a grasping element 100 is affixed to tissue distal to the target tissue 505, various means may be used to relocate the grasping element 100, and by connection, the tissue to which it is attached. In one example, depicted in FIG. 8A, one or more tethers 130 may be attached to the grasping element 100. As described previously, the tethers 130 may extend from the grasping element 100 to a delivery device, endoscope, or control mechanism. As shown in FIG. 8A, the tethers 130 may extend through the lumen of the anchor ring 300. The tethers 130 may be pulled or drawn proximally (see arrows in FIG. 8A), moving the grasping element 100 and target tissue 505 proximally. The tethers 130 may be pulled or drawn in such a way as to relocate the grasping element 100 and the target tissue 505 proximal to the anchor ring 300. This relocation may invert a length of the tissue tract 500, as will be described in detail below.

In another exemplary embodiment, as depicted in FIG. 8B, the operator may deploy forceps 520 or other clamping tool within the tissue tract 500. By securing the forceps 520 to the grasping element body 145, the operator may be able to pull the grasping element 100 proximally via the forceps 520 or other grasping or clamping tool. The grasping element 100 may be pulled or drawn in such a way as to relocate the grasping element 100 and the target tissue 505 proximal to the anchor ring.

In yet another exemplary embodiment, as depicted in FIGS. 9A-B, an inflatable grasping element 200 may be used to relocate the target tissue 505 proximally to a position proximal to the anchor ring 300, the anchor ring 300 being coupled to first tissue at surface 610. Referring to FIG. 9A, an inflatable grasping element 200 may be disposed in a tissue tract 500 via a delivery device 210, distal to the target tissue 505. In other embodiments, the inflatable grasping element 200 may be disposed proximal to the target tissue 505. After being deployed in the tissue tract 500, the inflatable grasping element 200 may transition to an expanded state, by transfer of air, inert gas, saline or other fluid to the space 220, as depicted in FIG. 9A. When in the expanded state, the exterior surface of outer wall 230 of the inflatable grasping element 200 may contact and affix to the wall 510 of the tissue tract 500.

After the inflatable grasping element 200 is affixed, or coupled, to the wall 510 of the tissue tract 500, some or all of the air, inert gas, saline, or other fluid in the space 220 may be evacuated via the delivery device 210. The evacuation of the fluid from the space 220 may revert the inflatable grasping element 200 to a collapsed state, as depicted in FIG. 9B. When the inflatable grasping element 200 reverts to a collapsed state after the outer wall 230 is coupled to the wall 510 of the tissue tract 500, the wall 510 retracts inward, maintaining contact with the outer wall 230. In this configuration, when the inflatable grasping element 200 is relocated proximally, the target tissue 505 will move with the inflatable grasping element 200. As is shown in FIG. 9B, the delivery device 210 passes through the lumen of the anchor ring 300. Therefore, when the inflatable grasping element 200 is relocated proximally to a position proximal to the anchor ring 300, the target tissue 505 may also be relocated proximally to a position proximal to the anchor ring 300. This relocation may invert a length of the tissue tract 500.

As described previously, the relocation of a grasping element 100 and target tissue 505 to a position proximal to the anchor ring 300 may invert a length of the tissue tract, as depicted in FIG. 10. The partially inverted tissue tract 600, includes regions where a second tissue 620 overlies and is radially inward of the anchor ring 300 and a first tissue 610.

In one or more embodiments of the present disclosure, a method of treating tissue may further comprise coupling a second ring to the first ring, with the second tissue between the first ring and the second ring. As shown in FIG. 11, an excision ring 400 may be disposed in the partially inverted tissue tract 600 via a delivery catheter or other delivery device. The excision ring 400 may be disposed at a same longitudinal position within the tissue tract as the anchor ring 300. The excision ring 400 may be disposed in the partially inverted tissue tract 600 in a collapsed state and then transitioned to an expanded state. When in an expanded state, the excision ring 400 may couple to the anchor ring 300 with the second tissue 620 between the anchor ring 300 and the excision ring 400.

Referring to FIG. 12, the coupling of excision ring 400 to anchor ring 300 with the second tissue 620 between the anchor ring 300 and the excision ring 400 is depicted. In one or more embodiments, the keying region 420 of the excision ring 400 interfaces and forms a mechanical interlock with the keying region 320 of the anchor ring 300. In some embodiments, the coupling of the excision ring 400 to the anchor ring 300 may cause the cutting edges 430 of the excision ring 400 to contact the cutting surface 330 of the anchor ring 300. When the cutting edges 430 contact the cutting surface 330, the edges 430 may cut the tissue between the cutting edges 430 and the cutting surface 330.

In other embodiments, another means may be deployed to cut tissue distal to the interlocking keying regions 320, 420 (e.g., distal to the second tissue 620 disposed between the anchor ring 300 and the excision ring 400). This other means may include blades, electrocautery devices, or other means of cutting tissue. In some embodiments, the section of tissue cut away from remaining tissue includes the target tissue 505. In one or more embodiments, the excision ring 400, while in an expanded state, forms a 360° arc of contact between the cutting edges 430 and cutting surface 330. In other embodiments, radial segments of the excision ring 430 comprise cutting edges 430 while other radial segments do not. In such embodiments, an operator may rotate the excision ring 400 about a luminal axis of excision ring 400 and the tissue tract, with respect to the anchor ring 300. In one or more of these methods of cutting tissue, the cutting of tissue may comprise a full-thickness resection.

After the excision ring 400 is coupled to the anchor ring 300, tissue may still be between the excision ring 400 and the anchor ring 300. The this tissue may heal with surrounding tissue or the bioabsorbable surfaces of anchor ring 300 or excision ring 400, forming a fused tissue tract 700, as depicted in FIG. 13. The two-ring complex may be left in the tract or may be removed at a later time. In other embodiments, the two-ring complex (e.g., an anchor ring 300 coupled to an excision ring 400) may comprise a bioabsorbable material that may either be absorbed into the subject or passed through the tissue tract of the subject. In one or more embodiments, the two-ring complex comprises a fluidic seal, as described previously.

FIG. 14 depicts a flow chart of an exemplary method 800 of treating tissue, according to the present disclosure. In the discussion below of exemplary methods and flow charts, reference may be made to the reference numerals detailed in FIGS. 1A-13. A first ring 300 may be coupled to a first tissue 610 of a wall 510 of a gastrointestinal tract 500 (step 810). A target tissue 505 may be proximally relocated to a position proximal to the first ring 300 so that second tissue 620 overlies the first ring 300 (step 820). A second ring 400 may be coupled to the first ring 300 with the second tissue 620 between the first ring 300 and the second ring 400 (step 830). One or more embodiments further comprise cutting tissue proximal to the second tissue 620 (step 840).

FIG. 15 depicts a flow chart of an exemplary method 900 of treating tissue, according to the present disclosure. A grasping element 100 may be coupled to a first section of an interior wall 510 of a tubular tissue 500 (step 910). Exemplary methods 900 may further comprise relocating the grasping element 100 proximally, thereby inverting a length of the tubular tissue 600 (step 920). In one or more embodiments, a method 900 for treating tissue further comprises cutting the wall 510 of the tubular tissue distal to the first section (step 930).

Although various embodiments of the present disclosure have been illustrated and described in detail, it will be readily apparent to those skilled in the art that various modifications may be made without departing from the present disclosure.

We claim:

1. A method of treating tissue, the method comprising:
   coupling a first ring to first tissue of a wall of a gastrointestinal tract, proximal to a target tissue;
   relocating the target tissue proximally to a position proximal to the first ring so that second tissue overlies the first ring; and
   coupling a second ring to the first ring, with the second tissue between the first ring and the second ring, wherein the coupling of the second ring to the first ring cuts tissue.

2. The method of claim 1, further comprising inserting an endoscope into the gastrointestinal tract.

3. The method of claim 1, further comprising deploying a grasping element to the wall of the gastrointestinal tract, distal to the target tissue.

4. The method of claim 3, wherein the grasping element comprises barbs, spikes, hooks, or other means for affixing to tissue.

5. The method of claim 3, wherein relocating the target tissue comprises relocating the grasping element from a position distal to the target tissue to a position proximal to the first ring.

6. The method of claim 1, wherein the tissue cut by the coupling of the second ring to the first ring is proximal to the second tissue.

7. The method of claim 6, wherein cutting tissue proximal to the second tissue comprises a full thickness resection.

8. The method of claim 1, wherein the coupling the second ring to the first ring forms a fluidic seal along the wall of the gastrointestinal tract.

9. The method of claim 1, wherein the first ring, the second ring, or both, comprise a radially expandable ring.

10. A method of treating tissue, the method comprising:
    coupling a grasping element to first tissue of a wall of a gastrointestinal tract, distal to a target tissue;
    coupling a ring to the wall of the gastrointestinal tract, proximal to the first tissue;
    relocating the first tissue to a location proximal to a second tissue, the target tissue being located between the first tissue and the second tissue; and
    coupling a second ring to the first ring, with tissue of the wall of the gastrointestinal tract between the first ring and the second ring.

11. The method of claim 10, further comprising cutting tissue between the second tissue and the target tissue.

12. The method of claim 11, wherein the cutting tissue comprises a full thickness resection.

13. The method of claim 10, further comprising removal of the target tissue from the gastrointestinal tract.

14. The method of claim 10, wherein the coupling of the second ring to the first ring forms a fluidic seal along the wall of the gastrointestinal tract.

15. A method of treating tissue, the method comprising:
    coupling a first ring to first tissue of a wall of a gastrointestinal tract, proximal to a target tissue;
    deploying a grasping element to the wall of the gastrointestinal tract, distal to the target tissue;

relocating the target tissue proximally to a position proximal to the first ring so that second tissue overlies the first ring, wherein relocating the target tissue comprises relocating the grasping element from a position distal to the target tissue to a position proximal to the first ring;

coupling a second ring to the first ring, with the second tissue between the first ring and the second ring; and cutting tissue proximal to the second tissue.

16. The method of claim 15, further comprising inserting an endoscope into the gastrointestinal tract.

17. The method of claim 15, wherein the grasping element comprises barbs, spikes, hooks, or other means for affixing to tissue.

18. The method of claim 15, wherein the coupling of the second ring to the first ring cuts tissue.

19. The method of claim 15, wherein cutting tissue proximal to the second tissue comprises a full thickness resection.

* * * * *